US00PP20733P2

(12) United States Plant Patent
Mowrey et al.

(10) Patent No.: US PP20,733 P2
(45) Date of Patent: Feb. 9, 2010

(54) STRAWBERRY PLANT NAMED 'DRISSTRAWNINE'

(50) Latin Name: *Fragaria×ananassa*
Varietal Denomination: DrisStrawNine

(75) Inventors: Bruce D. Mowrey, Watsonville, CA (US); Philip J. Stewart, Watsonville, CA (US); Martin P. Madesko, Watsonville, CA (US); JoAnne F. Coss, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/291,595

(22) Filed: Nov. 12, 2008

(51) Int. Cl.
*A01H 5/00* (2006.01)

(52) U.S. Cl. ..... Plt./209

(58) Field of Classification Search ..... Plt./209
See application file for complete search history.

*Primary Examiner*—Annette H Para
(74) *Attorney, Agent, or Firm*—Jondle & Associates, P.C.

(57) ABSTRACT

This invention relates to a new and distinct cultivar of strawberry plant named 'DrisStrawNine'. A new cultivar primarily characterized by its small hollow center, early to medium flowering time, everbearing fruit, low number of achenes per berry, and moderate resistance to Strawberry Mottle Virus is disclosed.

3 Drawing Sheets

Genus and species: *Fragaria×ananassa.*
Variety denomination: 'DrisStrawNine'.

BACKGROUND OF THE NEW PLANT

The present invention relates to a new and distinct strawberry cultivar designated 'DrisStrawNine' and botanically known as *Fragaria×ananassa*. This new strawberry cultivar was discovered in Summer, 2004 in Monterey, Calif. and originated from a cross between the female parent '94J283', a proprietary strawberry plant (unpatented) and the male parent '112H25', a proprietary strawberry plant (unpatented). The original seedling of the new cultivar was asexually propagated at a nursery in Monterey, Calif. 'DrisStrawNine' was subsequently asexually propagated and underwent further testing at a nursery in Monterey, Calif. for five years. The present invention has been found to retain its distinctive characteristics through successive asexual propagations.

DESCRIPTION OF THE PHOTOGRAPHS

The accompanying color photographs show typical specimens of the new cultivar at various stages of development as nearly true as it is possible to make in color reproductions. The photograph is of a plant about 7 months old.

DESCRIPTION OF THE NEW CULTIVAR

Figure 1:
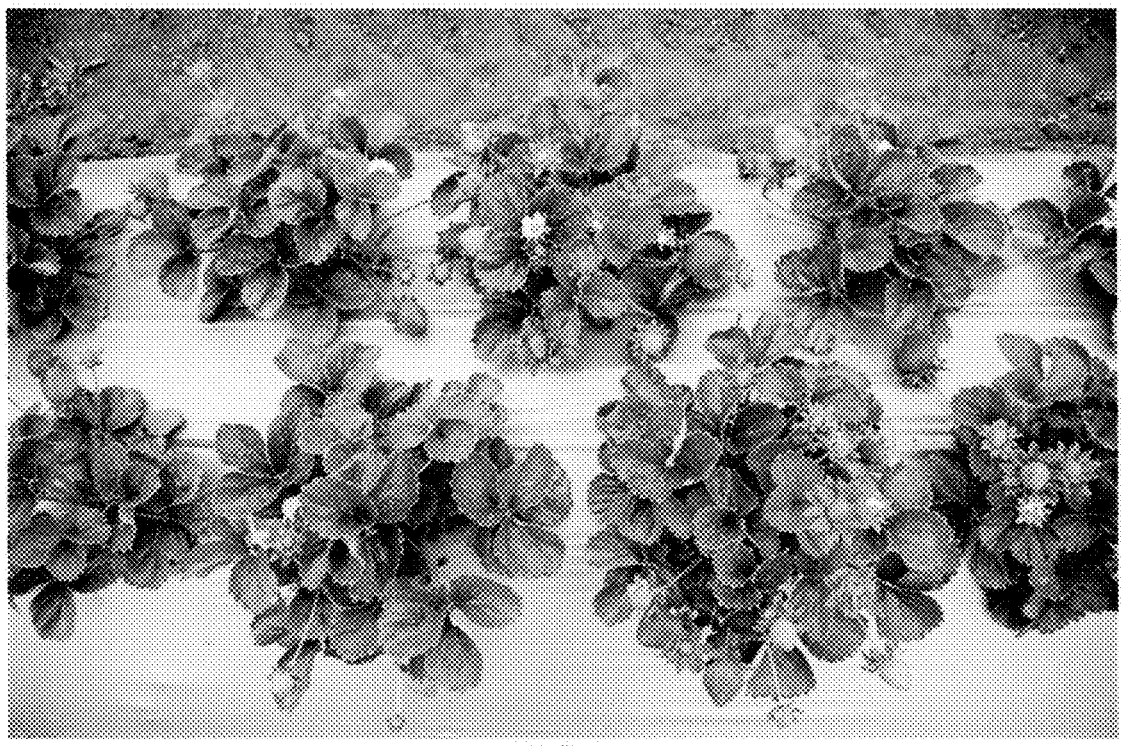
FIG. 1 shows overall plant habit including fruit at various stages of development.
Figure 2:
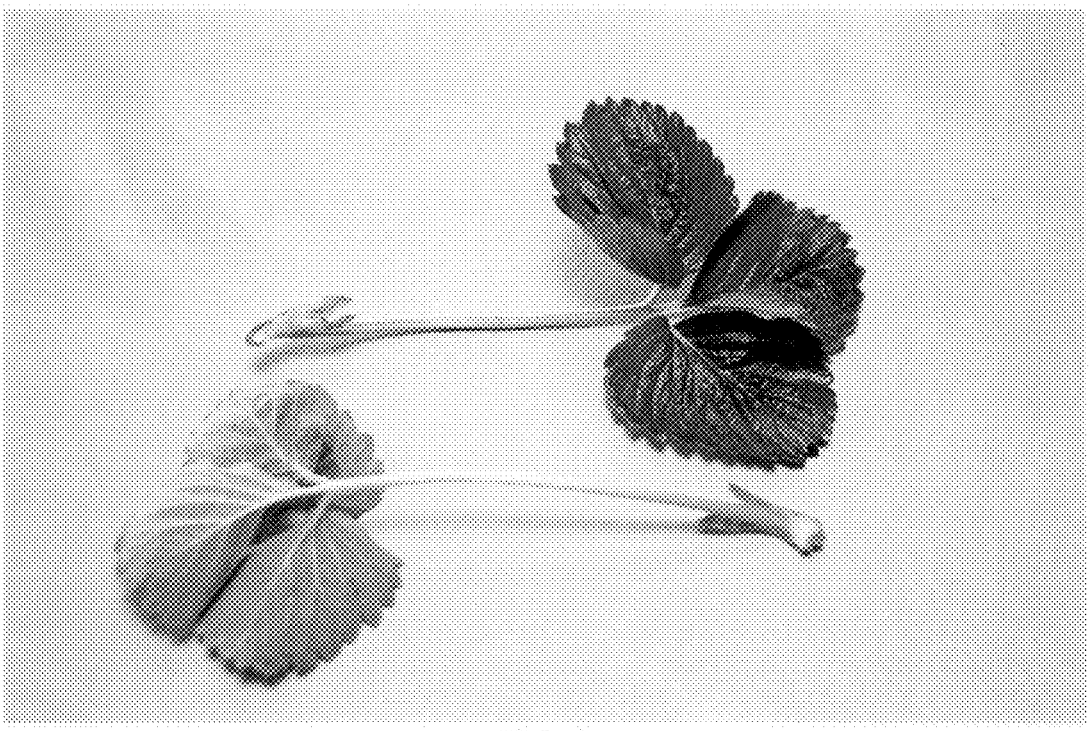
FIG. 2 shows leaves of the plant with three leaflets.
Figure 3:
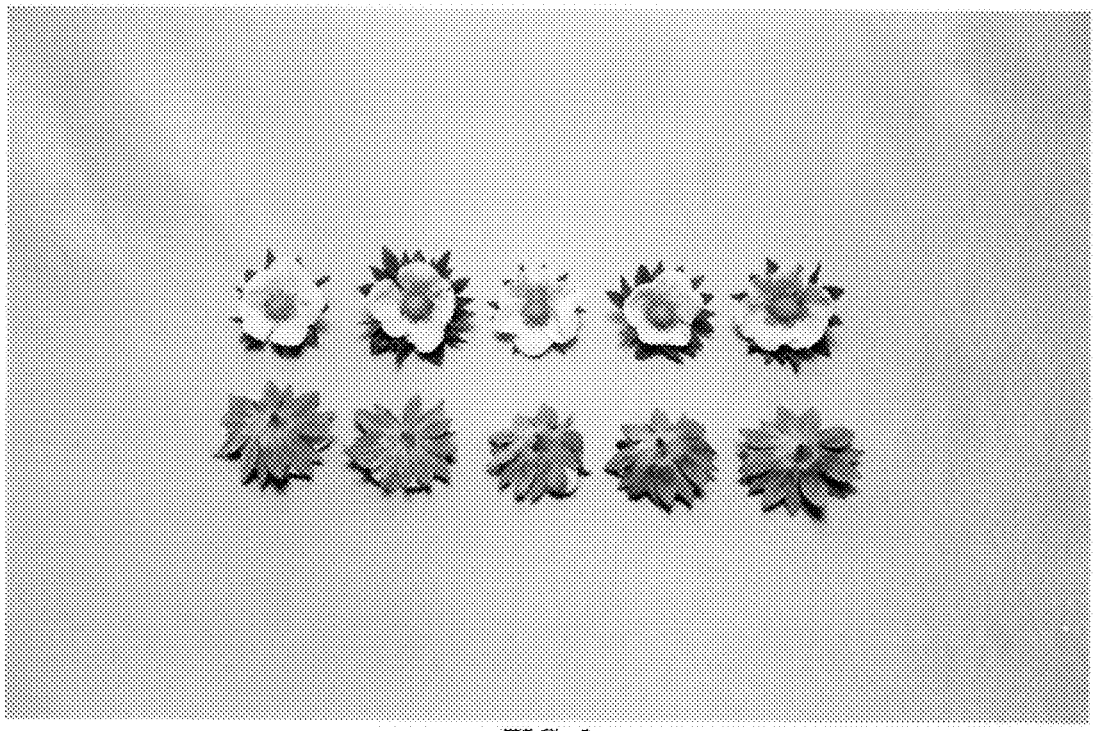
FIG. 3 shows both the upperside and underside of several of the flowers.
Figure 4:
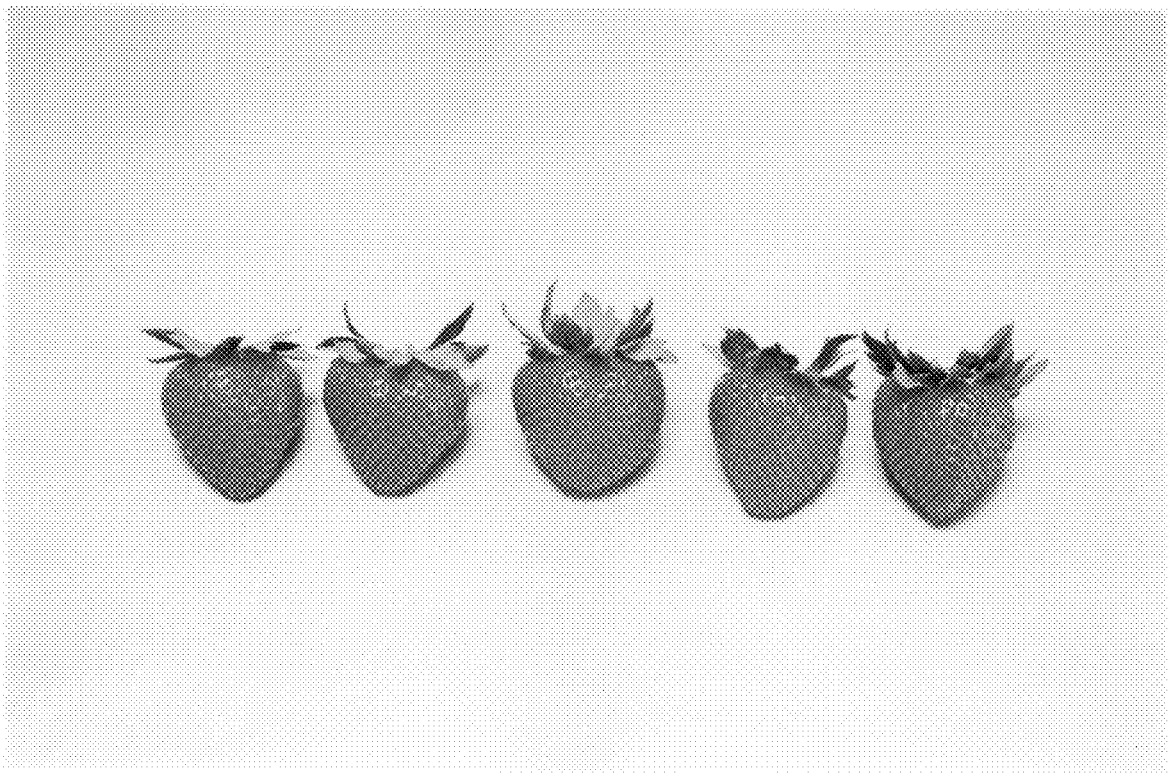
FIG. 4 shows the whole fruit.
Figure 5:
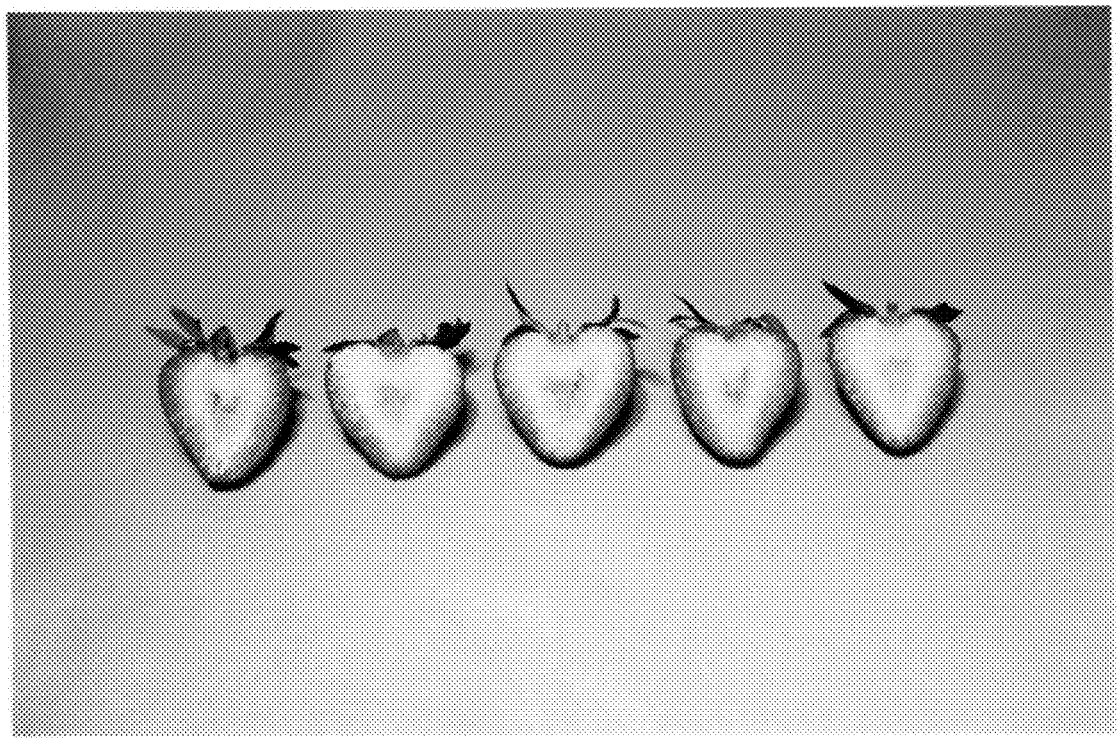
FIG. 5 shows the fruit in longitudinal cross-section.

The following description of 'DrisStrawNine' is based on observations taken from the 2004 to 2008 growing seasons in Monterey, Calif. This description is in accordance with UPOV terminology. Color designations, color descriptions, and other phenotypical descriptions may deviate from the stated values and descriptions depending upon variation in environmental, seasonal, climatic and cultural conditions. 'DrisStrawNine' has not been observed under all possible environmental conditions. Color terminology follows The Royal Horticultural Society Colour Chart, London (R.H.S.) (2001).

DETAILED BOTANICAL DESCRIPTION

Table 1 shows plant characteristics of the new variety compared with plant characteristics of the commercial varieties, 'Driscoll Lanai' (U.S. Plant Pat. No. 15,145) and 'San Juan' (U.S. Plant Pat. No. 12,899). Plant characteristics include plant height, diameter, number of crowns per plant, habit, density of individual plant and vigor.

TABLE 1

| Characteristic | 'DrisStrawNine' | 'Driscoll Lanai' | 'San Juan' |
|---|---|---|---|
| Plant height (cm) | 20.9 | 25.1 | 24.7 |
| Plant diameter (cm) | 32.9 | 36.5 | 38.9 |
| Number of crowns/plant | 3 | 3 | 3 |
| Habit | Upright | Flat globose | Globose |
| Density of individual plant | Medium | Medium | Between medium and dense |
| Vigor | Weak | Medium | Medium |

Table 2 shows leaf characteristics of the new cultivar compared with leaf characteristics of 'Driscoll Lanai' and 'San Juan'. Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, leaflet margin, leaflet shape, shape of leaf apex and shape of leaf base.

TABLE 2

| Leaf Characteristic | 'DrisStrawNine' | 'Driscoll Lanai' | 'San Juan' |
|---|---|---|---|
| Terminal leaflet length (cm) | 6.8 | 7.9 | 7.4 |
| Terminal leaflet width (cm) | 7.2 | 7.6 | 7.9 |
| Terminal leaflet length/width ratio | 1.0 | 1.0 | 0.9 |
| Terminal leaflet: length/width ratio | As long as broad | As long as broad | As long as broad |
| No. teeth/terminal leaflet | 24 | 23 | 25 |
| Shape of teeth | Rounded | Rounded | Rounded |
| Color of upperside of leaf | RHS 147A Dark yellow-green | RHS 147A Dark yellow-green | RHS 147A Dark yellow-green |
| Color of underside of leaf | RHS 147B Medium yellow-green | RHS 147C Medium yellow-green | RHS 147B Medium yellow-green |
| Leaf shape in cross section | Concave | Slightly concave | Concave |
| Leaf blistering | Medium | Medium | Weak |
| Leaf glossiness | Between medium and strong | Medium | Medium |
| No. leaflets | Three only | Three only | Three only |
| Terminal leaflet margin | Flat | Revolute | Revolute |
| Terminal leaflet shape | Orbicular | Orbicular | Orbicular |
| Terminal leaflet shape of base | Rounded | Rounded | Rounded |
| Terminal leaflet shape of apex | Rounded | Rounded | Rounded |

Table 3 shows information about the petiole, the petiolule, the bract, and the stipule of the new cultivar compared to 'Driscoll Lanai' and 'San Juan'. This includes petiole length in centimeters, petiole diameter in centimeters, petiolule length in centimeters, petiolule diameter in centimeters, bract frequency per petiole, stipule length in centimeters, stipule width in centimeters, stipule pubescence, petiole pubescence, pose of hairs on the petiole, color of the petiole, color of the petiolule and stipule anthocyanin coloration.

TABLE 3

| Characteristic | 'DrisStrawNine' | 'Driscoll Lanai' | 'San Juan' |
|---|---|---|---|
| Petiole length (cm) | 11.2 | 13.6 | 11.0 |
| Petiole diameter (cm) | 0.323 | 0.389 | 0.404 |
| Petiole pubescence | Dense | Dense | Dense |
| Petiole pose of hairs | Upwards | Outwards | Upwards |
| Petiole color | RHS 145A Medium yellow-green | RHS 144C Medium yellow-green | RHS 144C Medium yellow-green |
| Petiolule color | RHS 145B Medium yellow-green | RHS 144C Medium yellow-green | RHS 145A Medium yellow-green |
| Petiolule length (cm) | 0.826 | 1.203 | 0.734 |

TABLE 3-continued

| Characteristic | 'DrisStrawNine' | 'Driscoll Lanai' | 'San Juan' |
|---|---|---|---|
| Petiolule diameter (cm) | 0.158 | 0.151 | 0.177 |
| Bract frequency | 1 | 0 | 1 |
| Stipule length (cm) | 3.4 | 3.5 | 3.2 |
| Stipule width (cm) | 0.823 | 0.832 | 1.167 |
| Stipule pubescence | Medium | Dense | Dense |
| Stipule anthocyanin coloration | Absent to very weak | Absent to very weak | Absent to very weak |

Table 4 shows stolon characteristics of the new cultivar compared to 'Driscoll Lanai' and 'San Juan'. These characteristics include the number of stolons, average number of daughter plants, the anthocyanin coloration of the stolons, the thickness of the stolons, and the pubescence of the stolons.

TABLE 4

| Characteristic | 'DrisStrawNine' | 'Driscoll Lanai' | 'San Juan' |
|---|---|---|---|
| Stolon number | Medium | Many | Between medium and many |
| Average number of daughter plants | 35 | 17 | 57 |
| Stolon anthocyanin | Medium | Strong | Strong |
| Stolon thickness | Medium | Between medium and thick | Medium |
| Stolon pubescence | Sparse | Dense | Medium |

Table 5 shows inflorescence characteristics of the new cultivar compared to 'Driscoll Lanai' and 'San Juan'. These characteristics include inflorescence position relative to foliage, relative flower size, flower diameter in centimeters (measured from petal tip to petal tip), petal shape, petal apex shape, petal base shape, petal margin, relative spacing of petals, petal length in centimeters, petal width in centimeters, petal length to width ratio, typical number of petals observed, petal color, calyx diameter in centimeters (measured on back of flower from sepal tip to sepal tip), diameter of calyx relative to corolla, diameter of inner calyx relative to outer, sepal shape, sepal apex shape, sepal margin, sepal length in centimeters (measured from sepal tip to point of attachment to receptacle), sepal width in centimeters, typical number of sepals observed, receptacle color and anther color.

TABLE 5

| Characteristic | 'DrisStrawNine' | 'Driscoll Lanai' | 'San Juan' |
|---|---|---|---|
| Inflorescence position relative to foliage | Above | Above | Above |
| Flower size | Medium | Medium | Medium |
| Flower diameter (cm) | 2.920 | 2.835 | 2.850 |
| Petal shape | Orbicular | Orbicular | Orbicular |
| Petal apex | Rounded | Rounded | Rounded |
| Petal margin | Entire | Entire | Entire |
| Petal base shape | Concave-convex | Concave-convex | Concave-convex |

TABLE 5-continued

| Characteristic | 'DrisStrawNine' | 'Driscoll Lanai' | 'San Juan' |
|---|---|---|---|
| Petal spacing | Overlapping | Overlapping | Overlapping |
| Petal length (cm) | 1.257 | 1.133 | 1.227 |
| Petal width (cm) | 1.332 | 1.200 | 1.339 |
| Petal length/width ratio | 0.9 | 0.9 | 0.9 |
| Typical and observed petal number | 7 | 6 | 6 |
| Petal length/width ratio | As long as broad | Longer than broad | Longer than broad |
| Petal color | RHS 155B White | RHS 155B White | RHS 155C White |
| Calyx diameter (cm) | 3.573 | 3.647 | 3.969 |
| Calyx diameter relative to corolla | Larger | Between larger and much larger | Larger |
| Inner calyx diameter relative to outer | Same size | Same size | Same size |
| Sepal shape | Elliptical | Elliptical | Elliptical |
| Sepal apex | Convex | Convex | Convex |
| Sepal margin | Entire | Entire | Entire |
| Sepal length (cm) | 1.318 | 1.297 | 1.330 |
| Sepal width (cm) | 0.647 | 0.560 | 1.266 |
| Typical and observed sepal number | 14 | 13 | 13 |
| Receptacle color | RHS 2B Medium yellow | RHS 150B Medium yellow-green | RHS 2B Medium yellow |
| Anther color | RHS 22A Medium yellow-orange | RHS N167C Light greyed-orange | RHS 163B Medium greyed-orange |

Table 6 shows fruit characteristics of the new cultivar compared to 'Driscoll Lanai' and 'San Juan'.

TABLE 6

| Characteristic | 'DrisStrawNine' | 'Driscoll Lanai' | 'San Juan' |
|---|---|---|---|
| Fruiting truss length (cm) | 16.9 | 22.2 | 25.1 |
| Fruiting truss diameter (cm) | 0.512 | 0.360 | 0.481 |
| Number of berries per fruiting truss | 4 | 4 | 4 |
| Fruiting truss attitude | Semi-erect | Semi-erect | Semi-erect |
| Fruiting truss length | Medium | Long | Long |
| Truss color | RHS 144A Medium yellow-green | RHS 144A Medium yellow-green | RHS 144A Medium yellow-green |
| Fruit length (cm) | 4.274 | 4.327 | 4.857 |
| Fruit width (cm) | 4.222 | 4.431 | 4.603 |
| Fruit length/width ratio | 1.0 | 1.0 | 1.1 |
| Fruit length/width ratio | As long as broad | As long as broad | As long as broad |
| Fruit weight (g) | 23.1 | 25.6 | 28.0 |
| Relative fruit size | Medium | Medium | Large |
| Predominant fruit shape | Conical | Conical | Conical |

TABLE 6-continued

| Characteristic | 'DrisStrawNine' | 'Driscoll Lanai' | 'San Juan' |
|---|---|---|---|
| Difference in shape between primary & secondary fruits | Slight | Slight | Slight |
| Band without achenes | Narrow | Narrow | Narrow |
| Unevenness of fruit surface | Weak | Between medium and strong | Medium |
| Fruit skin color | RHS 46A Dark red | RHS 46A Dark red | RHS 53A Dark red |
| Evenness of fruit color | Even | Even | Even |
| Fruit glossiness | Medium | Medium | Between medium and strong |
| Insertion of achenes | Level with surface | Above surface | Below surface |
| Achene coloration-sunward side of berry | RHS 184A Dark greyed-purple | RHS 183C Dark greyed-purple | RHS 180B Dark greyed-red |
| Achene coloration-shaded side of berry | RHS 153B Medium yellow-green | RHS 152B medium yellow-green | RHS 150B light yellow-green |
| Achenes per berry | 320 | 345 | 397 |
| Achene weight (g) | 0.0005525 | 0.000497336 | 0.000558419 |
| Insertion of calyx | Level | Level | Level |
| Pose of calyx segments | Spreading | Reflexed | Reflexed |
| Size of calyx in relation to fruit | Larger | Larger | Between smaller and same size |
| Adherence of calyx | Strong | Medium | Strong |
| Firmness of flesh | Medium | Medium | Firm |
| Color of the flesh | RHS 155C White and RHS 41A medium red | RHS 155A White and RHS 41B medium red | RHS 155B White and RHS 41A medium red |
| Evenness of flesh color | Uneven | Slightly uneven | Slightly uneven |
| Distribution of flesh color | Marginal and central | Marginal and central | Marginal and central |
| Fruit hollow length (cm) | 1.341 | 2.055 | 2.169 |
| Fruit hollow width (cm) | 1.023 | 0.774 | 0.738 |
| Fruit hollow length/width ratio | 1.3 | 2.7 | 2.9 |
| Hollow center | Small | Medium | Small |
| Sweetness | Medium | Medium | Strong |
| Acidity | Medium | Medium | Weak |
| Texture when tasted | Medium | Medium | Fine |
| Time of flowering | Between early and medium | Between early and medium | Between early and medium |
| Harvest maturity (50% of plants with ripe fruit) | Late March to early November | Late March to early November | Late March to early November |
| Type of bearing | Fully everbearing | Partially everbearing | Partially everbearing |
| Grams of fruit/plant | 1,505 | 1,609 | 1,412 |

Table 7 shows pest and disease characteristics of the new cultivar compared to 'Driscoll Lanai' and 'San Juan'.

TABLE 7

| Pest or Disease | 'DrisStrawNine' | 'Driscoll Lanai' | 'San Juan' |
|---|---|---|---|
| *Tetranychus urticae* (2-spotted spider mite) | Moderately susceptible | Susceptible | Moderately susceptible |
| *Botrytis* fruit rot | Susceptible | Susceptible | Susceptible |
| Powdery mildew | Between moderately susceptible and susceptible | Susceptible | Susceptible |

TABLE 7-continued

| Pest or Disease | 'DrisStrawNine' | 'Driscoll Lanai' | 'San Juan' |
|---|---|---|---|
| *Verticillium* wilt | Susceptible | Moderately susceptible | Susceptible |
| Viral diseases-Strawberry Mottle Virus | Moderately resistant | Moderately resistant | Moderately resistant |
| *Xanthomonas fragariae* | Moderately susceptible | Moderately susceptible | Moderately susceptible |

We claim:

1. A new and distinct cultivar of strawberry plant, as described and shown herein.

* * * * *